United States Patent [19]

Kane

[11] 4,254,291

[45] Mar. 3, 1981

[54] ALLYLIC REARRANGEMENT PROCESS

[75] Inventor: Bernard J. Kane, Atlantic Beach, Fla.

[73] Assignee: SCM Corporation, New York, N.Y.

[21] Appl. No.: 68,507

[22] Filed: Aug. 22, 1979

Related U.S. Application Data

[63] Continuation-in-part of Ser. No. 966,635, Dec. 5, 1978, abandoned.

[51] Int. Cl.³ .................... C07C 33/02; C07C 35/18; C07C 29/56; C07F 5/04
[52] U.S. Cl. .................. 568/875; 260/462 R; 568/825; 568/902
[58] Field of Search ............. 568/875, 825, 902; 260/462 R

[56] References Cited

U.S. PATENT DOCUMENTS

| | | |
|---|---|---|
| 2,587,753 | 3/1952 | O'Connor et al. ............. 568/923 |
| 3,244,752 | 4/1966 | Eschinasi ..................... 568/875 |
| 3,344,171 | 9/1967 | Lemberg ....................... 568/875 |
| 3,925,485 | 12/1975 | Chabardes et al. ........... 568/875 |
| 3,927,076 | 12/1975 | Babler .......................... 568/715 |
| 3,947,504 | 3/1976 | Kyo et al. ..................... 568/923 |
| 3,997,577 | 12/1976 | Fraunberg .................... 568/875 |
| 4,006,193 | 2/1977 | Ninagawa et al. ............ 568/875 |
| 4,122,291 | 10/1978 | Kyo et al. .................... 260/462 R |

FOREIGN PATENT DOCUMENTS

| | | |
|---|---|---|
| 1599581 | 8/1970 | France . |
| 50-52011 | 5/1975 | Japan .................... 568/906 |
| 50-58004 | 5/1975 | Japan .................... 568/906 |
| 252570 | 6/1926 | United Kingdom . |

OTHER PUBLICATIONS

Rivkin et al., "Zh. Obshch. Khim.", 5, pp. 274–276, (1935).
Chabardes et al., "Tetrahydron," vol. 33, pp. 1775–1783 (1977).
Bessiere et al., "J. Chem. Research" (S), 1977, pp. 304 and 305.

Primary Examiner—Joseph E. Evans
Attorney, Agent, or Firm—Robert A. Sturges; Merton H. Douthitt

[57] ABSTRACT

A process for allylic rearrangement, particularly terpenoid allylic rearrangement, utilizing certain acid forming metals to form an ester or alcoholate (alcohologen) of the allylic alcohol to be rearranged, isomerizing and cleaving the alcohologen in the presence of a transition metal compound catalyst and recovering the rearranged alcohol.

41 Claims, 2 Drawing Figures

ALLYLIC REARRANGEMENT PROCESS

RELATED APPLICATION

This application is a continuation-in-part of my copending application Ser. No. 966,635 filed Dec. 5, 1978, now abandoned.

BACKGROUND AND PRIOR ART

The instant invention relates to a process for enhancing allylic rearrangement beyond the equilibrium between an allylic primary or secondary alcohol and an allylic tertiary alcohol that is attainable in the liquid phase rearrangement of an allylic tertiary alcohol to an allylic primary or secondary alcohol at modest temperature (generally between 50° and 250° C. and advantageously between 100° and 200° C.) in the presence of a catalyst comprising a metal of Group Va, VIa, or VIIa of the Periodic Table of Mendeleev. Such are the liquid phase catalystic allylic tertiary alcohol isomerization conditions referred to herein, and they are taught in U.S. Pat. No. 3,925,485 (Chabardes et al) and again in U.S. Pat. No. 4,006,193 (Ninagawa et al). The teachings of both these patents are incorporated herein be reference. Charbardes et al exemplify use of temperatures such as 150°, 160° and 161° C. to so rearrange linalool into geraniol and nerol. The equilibrium obtained in such operation is roughly 30% of these primary alcohols and 70% of the tertiary alcohol. Nerol is a geometric isomer of geraniol.

BRIEF SUMMARY OF THE INVENTION

In the instant process one forms an isomerization reaction mixture containing an allyic tertiary "alcohologen" (an alcohologen being a compound containing no catalyst metal, but one that is cleavable to yield the alcohol to which it corresponds). One isomerizes said allylic tertiary alcohologen under liquid phase catalytic allylic tertiary alcohol isomerization conditions (broadly those shown by Chabardes et al, above, with respect to temperature and catalyst) until the allylic radicals or residues, including those of free allylic alcohols, if present, remaining in the mixture are richer in allylic primary or secondary conformation than in allylic tertiary conformation—in other words the isomerization of such residues surpasses the customary equilibrium between the corresponding allylic alcohols obtainable by use of the processes of either Chabardes et al or Ninagawa et al. Making the alcohologen also enables one to operate advantageously under atmospheric pressure at slightly higher temperatures (e.g. 160°–180° for geraniol-nerol from linalool) than those exemplified by Chabardes et al. An attendant advantage is speed in addition to completeness of reaction.

While the instant invention should by no means be construed only as a liquid phase catalytic process for making allylic primary or secondary alcohols from allylic tertiary alcohols, such products are perhaps the ones most readily marketable in quantity. One might characterize the instant invention as the forming of allylic alcohologens prior to or during the liquid phase catalytic isomerization of the allylic tertiary moieties of the various allylic compounds present into primary of secondary allylic moieties.

In one principal aspect of this invention allylic tertiary alcohologen (such as a linalyl isobutyl borate) is preformed, then this material is subjected to the catalystic liquid phase isomerization. In such isomerization free tertiary alcohol does not appear to exert any significant effect, and, if it is present, it appears to be independent of the amount of free alcohol present; the reaction is zero order with respect to the free tertiary alcohol.

In another principal aspect of this invention allylic tertiary alcohologens (such as a linalyl isobutyl borate) is formed by collateral reaction (e.g. by transesterification of an isobutyl borate) while free allylic tertiary alcohol (e.g. linalool) also is isomerizing into free allylic primary or secondary alcohol (e.g., geraniol and nerol), and allylic primary or secondary alcohologens (e.g., geranyl and neryl borates) also are being formed concurrently.

Clearly one can "hybridize" these two aspects in various ways, starting the isomerizing with more or less of preformed allylic tertiary alcohologen and of the corresponding free allylic tertiary alcohol. In an extreme case of said another principal aspect, above, it could be possible that only a modest proportion of allylic tertiary alcohologen relative to free allylic primary or secondary alcohol is formed, and such products convert to their particular alcohologens in the operation.

As one of the most important applications of this invention is to convert linalool into geraniol and nerol (the mol ratio of geraniol to nerol being about 1.63:1), this application will from time to time refer to "linaloologen", "geraniologen," and "nerologen". These terms mean an alcohologen which yields linalool, geraniol, and nerol, respectively. Analogously to "butanologen" yields butanol by cleavage; and an isobutanol-linalyl mixed ester of a polybasic acid such as boric acid could be both "isobutanologenic" and "linaloologenic," although, for purposes of this specification, it will be termed a "linaloologen" or "allylic tertiary alcohologen" (because the alkanol cleavage product is considered as a byproduct that ordinarily would be recovered for reuse in the isomerization).

BRIEF DESCRIPTION OF THE DRAWINGS

The drawings are process flow diagrams outlining two main adaptations of the instant invention for possible commercial production. In the drawings pumps, compressors, ejectors, instruments, valves and fittings, agitators, and heaters are not shown. They can be provided in conventional manner where necessary or desirable. Both drawings figures will be described in connection with the production of geraniol and nerol from linalool although similar operations can be practiced with other volatile tertiary allylic alcohol starting materials.

DETAILED DESCRIPTION OF THE INVENTION

Figure 1:
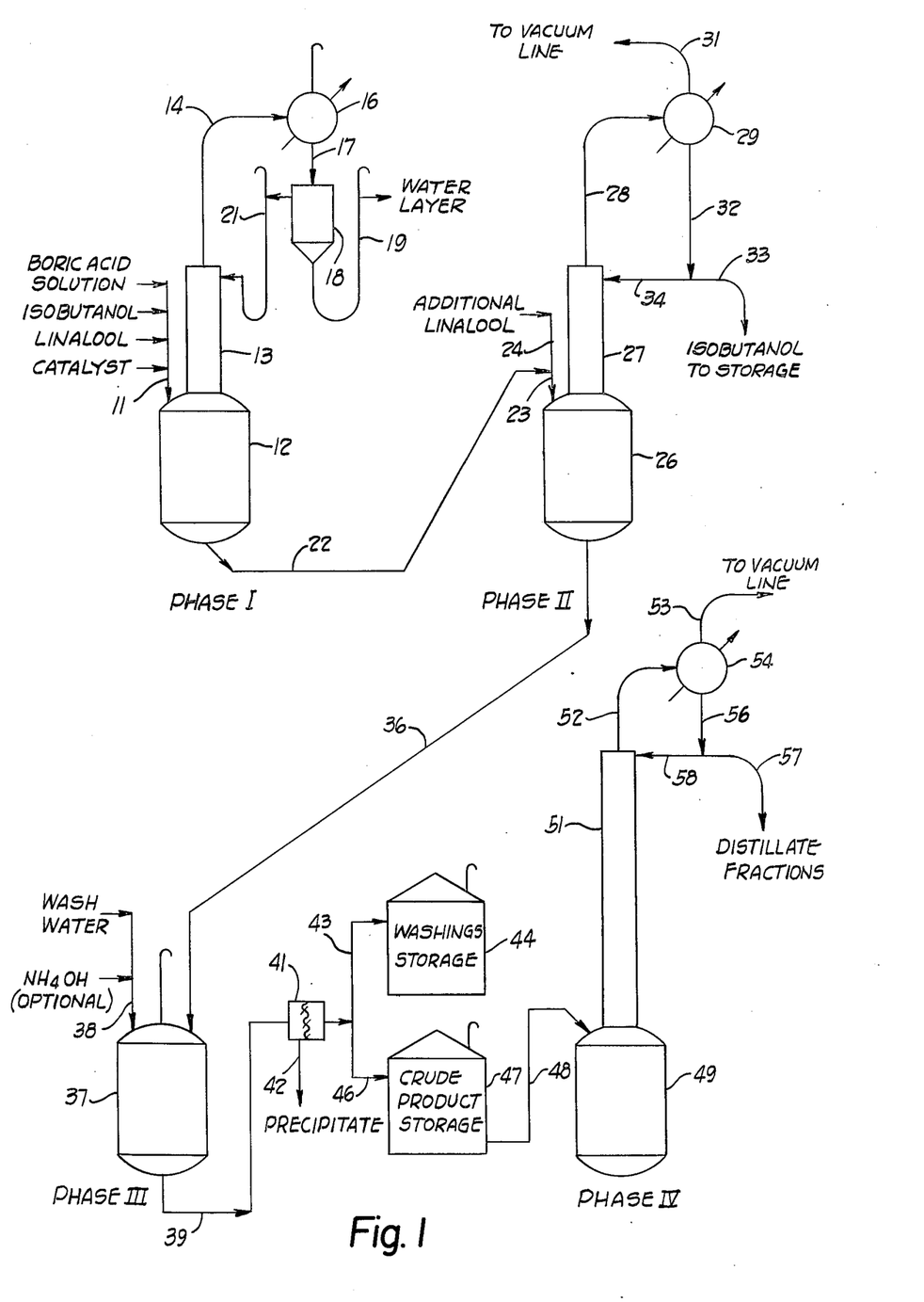

In the adaptation depicted in FIG. 1 linaloolgen is made in a reaction that is collateral to the following isomerizations (which are occurring concurrently):
(a) linalool to geraniol and nerol; and (b) such linaloologen is formed to geraniologen and nerologen. These alcohologens are various orthoborates of linalool and geraniol. In addition to forming linaloologen which isomerizes into geraniologen and nerologen, the geraniol and nerol formed from isomerization of linalool here form geraniologen and nerologen. This helps to drive the isomerization of linalool to the right, i.e., to isomer products.

Figure 2:
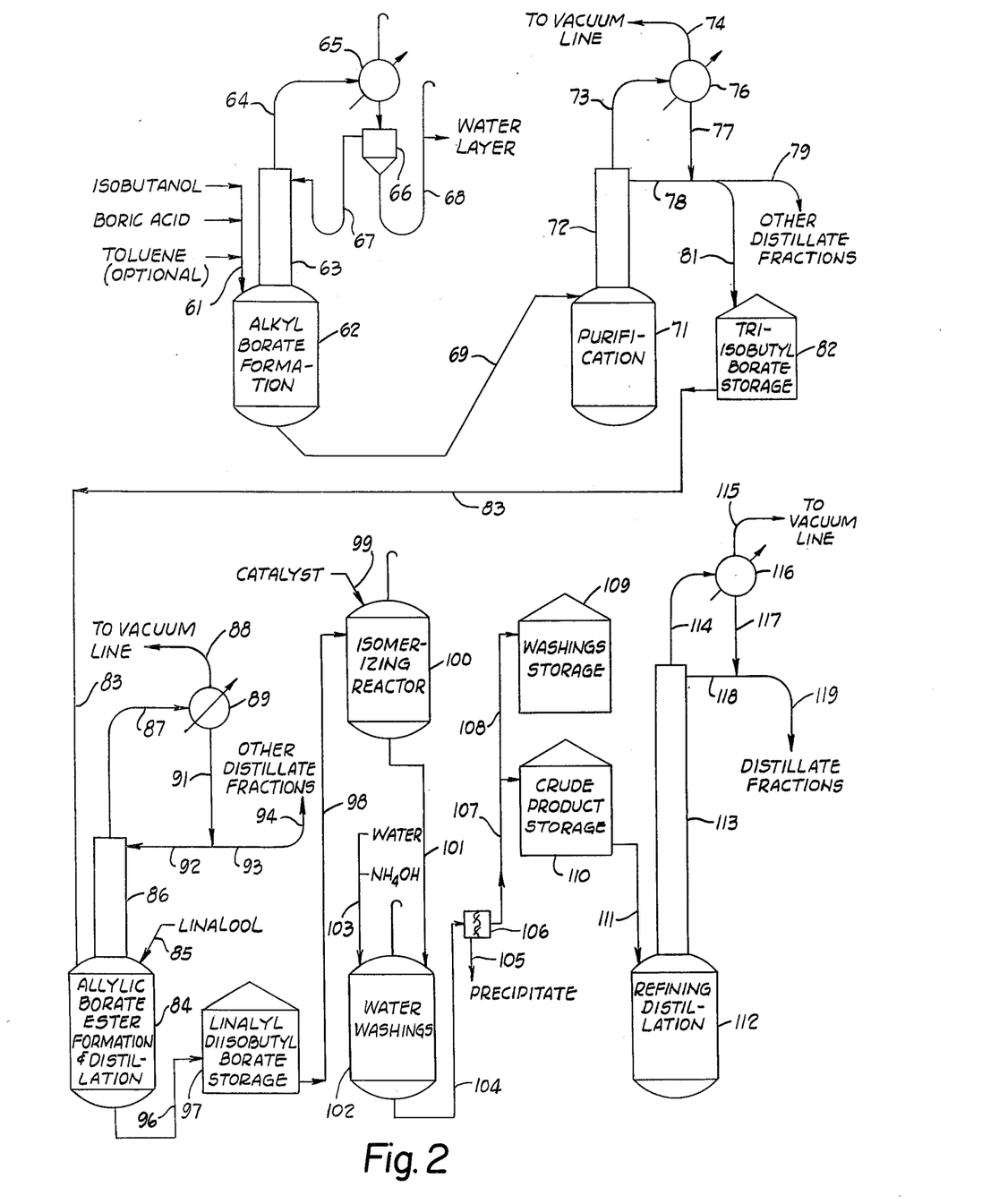

In the adaptation depicted in FIG. 2 linaloologen is preformed as a linalyl orthoborate, and such allylic alchologen is isomerized to geranyl and neryl counterpart alchologens.

Referring specifically now to FIG. 1, this figure is the basis for design of a pilot plant for utilizing up to about 1500 pounds per day of a technical grade linalool (at least about 30% purity and even up to 95–98% purity). The linalool feed in this instance is only 48% linalool. The remainder of such feed is almost exclusively cyclic, non-allylic terpene alcohols such as fenchol, plinols, 2-pinanols, and a minute amount of alpha terpineol. The instant invention can use such a feed advantageously because the isomerizations occuring appear to be restricted to the tertiary allylic material, and the customary impurities that are difficult to separate from linalool are unreactive here. Those materials in the linalool feed that are difficult to separate from nerol and geraniol, but are readily separable from linalool (e.g., most of the alpha-terpineol) are, of course, advantageously removed from the linalool feed. Because the instant process can be operated to get, for example, much more geraniol and nerol from linalool than the reference processes, use of fairly dilute feed can be economic. At least part of the customary impurities can be recovered economically for reuse, e.g. 2-pinanols. Typically the linalool feed can be derived conventionally from alpha-pinene (preferably) or betapinene.

Additionally, side reactions in the reference process can cause deterioration of allylic primary and secondary alcohol products (probably through the route of unsaturated aldehyde formation, which aldehyde is unstable at 140°–160° C. and leads to the formation of dimeric aldol condensation products). In the instant processing alchologens are not as subject to such deterioration at such temperature, and this can lead to much improved yields.

Referring to FIG. 1, kettle 12 has a heating and cooling jacket and is fitted with an agitator. It also can have internal heating and cooling coils, if desired or necessary. Aqueous 20% boric acid, 1087 parts of isobutanol, 1000 parts of the 48% linalool (a "very lean" technical grade) and 2 parts of ammonium metavanadate catalyst are charged to kettle 12, along with 700 parts of toluene. Part of or all of the boric acid solution used can be recovered from previous similar operations.

The kettle contents are agitated and heated. Vapors therefrom ascend fractional distillation column 13. This column is irrigated at the top with a flow of separated organic phase reflux from line 21. Distillate vapors pass through line 14 and are condensed in condenser 16. Condenser 16 is indirectly water-cooled and vented to atmosphere. Condensate flows through line 17 into decanter 18. Herein it separates by gravity into an upper organic-rich phase and a lower aqueous phase (a "water layer"). This water layer, containing about 2% isobutanol, is drawn from the bottom of decanter 18 through line 19. Such layer is 2022 parts, and it is reserved for washing crude product in Phase III of the operation. Following the water removal, 485 parts of a mixture of toluene and isobutanol are withdrawn from line 21 as condensed distillate (by an outlet not shown) instead of being returned to reflux column 13.

In this first phase, Phase I, not only is water removed, but also isobutyl borates are made along with some linalyl-butyl borates, some geranyl and neryl borates and some free geraniol and nerol. The temperature of the distilling operation goes from 90° C. for the removal of the water, then to 160° ultimately in 14 hours total of heating. The pressure of the operation is atmospheric.

The operation is shielded from atmosphere by a purge of nitrogen gas removed through the vent over the condenser.

The second Phase of the operation commences by charging kettle 26 with 2080 parts of additional linalool entering line 24 and inlet 23 and the liquid product of Phase I removed from kettle 12. The latter is transferred through line 22 and inlet 23. Kettle 26 is provided with internal heating coils. Vapors from the kettle ascend fractional distillation column 27, line 28, are condensed in condenser 29, and the condensate passes through line 32 with provision for column reflux through line 34 and distillate collection through line 33. Various distillate fractions are sent to storage not shown. Initially the condenser is vented to atmosphere. When lower absolute pressures are used, line 31 is connected to a vacuum line.

As this distallation proceeds, the total pressure over it is gradually reduced to maintain temperature of 160° C. in the kettle. This removes most of the isobutanol which is sent to storage through line 33 with a relatively low reflux being used in line 34. This isobutanol consists of 1170 parts containing a small amount of toluene. It is saved for reuse.

Kettle 26 is boiled for 12 more hours at 200 mm Hg abs whereupon the temperature herein reached at 170° C. Eight hours more boiling at 200 mm provides a kettle temperature of 174°. An analysis of the allylic alcohols in the kettle at this point is about 10.9% linalool and 90.1% nerol and geraniol when a sample is hydrolyzed.

The third Phase commences with transfer of the stripped contents of kettle 26 into kettle 37, which is vented to atmosphere and is equipped with an agitator and heating means not shown. Herein the crude product is washed at 85° C. three times successively by agitation with aqueous material, settlement each time, and drawing off the settled aqueous layer each time ("water layer"). The first wash is done with a 1652 parts of water, preferably of aqueous material, reserved from Phase I and drawn off decanter 18 by line 19. The second wash is 400 parts of water and/or such aqueous material, as is the third wash. The third wash optionally can be 400 parts of 7% ammonium hydroxide in lieu of water. The settled washings are drawn off kettle 37 through line 39 and filtered in filter 41. A minute amount of precipitation, less than one part is removed from the operation through outlet 42. This sediment is vanadium-bearing material. Filtered washings containing about 14.7% dissolved boric acid are stored in washings storage tank 44 (2798 parts) before reuse in a new Phase I.

The crude product is the upper or oily layer. It is withdrawn from kettle 37 through line 39 and filtered though filter 41 with any precipitate removal being removed from the operation through outlet 42. The filtered crude product enters crude product storage tank 47 through line 46. This is 3217 parts.

The stored curde product, 3217 parts, and three parts of potassium stearate are transferred through line 48 into still pot 49 to start Phase IV, a refining distillation. The contents of the product are heated indirectly by means not shown. Vapors ascend though fractional distillation column 51, line 52, and are condensed in water-cooled water condenser 54. Condensate drains through line 56 and refluxing the column through line 58 and withdrawal of distillate fractions through line 57. Initially the condenser is vented to atmosphere to take a small forecut of isobutanol and water. For good odor and good quality of the product alcohols the pot temperature is limited to 140° C. except for final residue-stripping operations when the temperature is allowed to go as high as 170°. Accordingly, during the distilling operation total pressure is reduced in stages to maintain the 140° C. pot temperature.

These stages ordinarily are, starting with atmospheric, 100 mm. Hg abs. when the pot reaches 140° C., then 10 mm. Hg abs. when the pot again reaches 140° C., and finally 1 mm. or less mm. Hg. abs. for stripping values from the residue.

The cuts are as follows: forecut 449 parts isobutyl alcohol and 103 parts water; "waste" cut of 252 parts mainly hydrocarbons; a cut predominantly of various alcohols weighing 334 parts and containing 10.3% linalool, the other alcohols being considered primarily impurities for the purpose of this operation, an intermediate cut of 642 parts containing 23% linalool; an intermediate nerol plus geraniol cut of 152 parts containing about 80% of those alcohols and being reserved for recycling to a subsequent purifying distillation; a main product cut of 1062 parts containing 99% nerol and geraniol; and a further cut of 25 parts of high purity of nerol and geraniol, but usually slightly off in odor or in color, this cut also being recycled for redistillation. From the "waste" cut and afterwards the pressure at the top of the column is maintained at 10 mm. Hg. abs. except for the last recycled cut, which is derived from the stripping operation previously described. Still residues weighed 191 parts.

The fractional distilling columns in connection with both FIGS. 1 and 2 are conventionally packed towers, although there could be various other types such as sieve plates, etc. Packed columns here are preferred for their low pressure drop. The preferred material of construction for the equipment described herein is austenitic stainless steel, but glass-lined steel, monel metal and other corrosion-resistant materials also can be used with very good effect for precluding unnecessary contamination of the fragrance materials being handled.

Except for the final purification, it should be evident that a "one-pot" operation could be practiced wherein said "pot" or kettle was equipped for heating and cooling with agitation under atmospheric and reduced pressure, also could be used as a water wash vessel, and was arranged also for fractional distillation therefrom with decantation and distillate fraction handling.

Reference now is made to FIG. 2 wherein the linalool feed is a 95% purity technical grade described more fully in connection with examples which follow.

The equipment for this operation in many instances can be essentially like that for the operation described in FIG. 1 with adjustments to inlets and outlets. Kettle 62 and appurtenant equipment of FIG. 2 is like kettle 26 and its appurtenances of FIG. 1; water wash vessel 102 can be identical to like vessel 37 of FIG. 1; refining distillation pot 112 and its appurtenant equipment of FIG. 2 can be essentially the same as the refining distillation pot 49 and its appurtenant equipment of FIG. 1.

Kettle 62 is charged with 975 parts of isobutanol, 252 parts of anhydrous boric acid, and 500 parts of toluene through line 61. The kettle contents are agitated and heated. The vapors therefrom ascend fractional distillation column 63. Water of reaction and toluene distill off through column 63 and line 64. The vapors are condensed by condenser 65. Condensate flows from the condenser into decanter 66. Herein toluene separates and is returned as reflux to the top of the column through line 67. A water layer of 228 parts is withdrawn from the decanter through line 68. This layer contains about 2% isobutanol. The operation takes approximately 10 hours, and the kettle temperature gradually rises during this period from about 94° to 134° C. The operation is at atmospheric pressure. The product, 1513 parts of crude triisobutyl borate, is transferred from kettle 62 through line 69 into kettle 71.

In this purification operation the contents of kettle 71 are boiled with the vapors ascending fractional distillation column 72, line 73, and being condensed in condenser 76. The condenser initially is vented to atmosphere and can be connected to a vacuum line by connection 74. Condensate flows through lines 77 and 78 to reflux column 72. Part of the condensate is withdrawn through line 79 as other distillate fractions which are sent to storage now shown. Triisobutyl borate is distilled at 10 mm. Hg. Abs. and stored in tank 82. It boils at about 105°–106° C. under this pressure, and there are 805 parts of it.

Said other distillate fractions first taken are a mixture of toluene and isobutanol, 567 parts (taken at atmospheric pressure and 100 mm. Hg abs.) and a recycle intermediate cut rich in triisobutyl borate (104 parts). The latter cut is taken at 10 mm. Hg. abs. The kettle temperature is not permitted to rise above about 140°–150° C., but the product is very stable to heat deterioration, accordingly, higher temperature might very well be used. A residue of 9 parts is drained from kettle 71 by an outlet not shown.

250 parts of triisobutyl borate from storage tank 82 is transferred through line 83 into kettle 84. Kettle 84 is charged with 150 parts of linalool through line 85. The mixed contents of kettle 84 are boiled up. Vapors ascend fractional distillation column 86 and line 87. They are condensed in condenser 89. Reduced pressure is maintained in the apparatus by connection 88 to a vacuum line. Condensate from the condensor returns by lines 91 and 92 to reflux the distilling column. Distillate fractions are taken through line 94. The pot temperature is 150° C., and the first distillate fraction of 50 parts is taken at 100 mm. Hg abs. pressure. The second fraction of 112 parts at the same pot temperature is taken at 10 mm. Hg. abs. pressure. Linalyl diisobutyl borate, 238 parts, is transferred through line 96 into storage tank 97.

50 parts of linalyl diisobutyl borate are drawn from storage through line 98 and charged into reactor 100. Through line 99 there is also charged one part of catalyst, specifically the orthovanadate ester of triethanolamine. This operation is vented and can be blanketed with nitrogen to preclude possible atmospheric contamination. The materials in reactor 100 are heated to 160°–165° C. with agitation for 2 hours. At this point the reactor contents are transferred to water washing vessel 102 using line 101. The water washing in vessel 102 is like that previously described for the operation of vessel 37 of FIG. 1, except that more fresh water would be used because of the use of anhydrous boric acid in this FIG. 2 operation. (The boric acid can be used as a solution or as a dry crystal or as an aqueous slurry, and it can be recovered or fresh, or a mixture of both.) The filtration with filter 106 is like the filtration with filter 41 of FIG. 1. Filtered washings go through line 108 to storage tank 109, and the crude allylic alcohol product goes through line 107 to to storage tank 110. The crude product analysis is 16.95% linalool, 32.80% nerol, and 50.25% geraniol, the nerol and geraniol amounting to 83.05%.

Pot 112 is charged with the crude product line 111. The refining distillation is conducted using pot 112 and its appurtenant equipment in a manner quite like that described in connection with pot 49 and its appurtenant equipment of FIG. 1.

DETAILED DESCRIPTION OF THE INVENTION

The catalysts which can be used in the process of this invention are compounds of the transition metals found in Groups Va, VIa, VIIa of the Periodic Table of Mendeleev. Useful catalysts are described in reasonable detail in the Chabardes et al U.S. Pat. No. 3,925,485, and such patent even shows promoters for the catalysis. Preferably, the catalysts are derivatives of metals selected from the group consisting of vanadium, niobium, molybdenum, tungsten, rhenium, and chromium. In particular the most highly preferred catalysts here are vanadic esters such as ethyl orthovanadate, butyl orthovanadate, n-hexyl orthovanadate, the orthovanadate ester of triethanolamine, and ammonium metavanadate.

The proportion of catalyst used per unit weight of allylic tertiary alcohol charged to a reactor here usually is more than 0.001% and preferably is between 0.5 and about 2.0% of such alcohol. For proportioning catalyst to a preformed alcohologen, the catalyst proportion is based on the allylic tertiary alcohol equivalent of such alcohologen. When fractionally distilling crude allylic alcohol product, catalyst should not be present. This is to preclude reversion of some product to allylic tertiary alcohol.

Anything that generates strong acid in the operation usually is deleterious to allylic alcohols. Accordingly, such things desirably are avoided. It is preferred to avoid the presence of unstable halogenated or sulfate substances for this reason. Certain of the useful catalysts require an induction period to permit at least part of their substance to become miscible in the reaction mixture before operating with highest activity.

The instant isomerization desirably is carried out at a temperature broadly between about 50° and about 250° C., (and even 275° is possible without being too deleterious when using a gentle catalyst such as 1% hexyl orthovanadate or less and a stable alcohologen such as linalyl orthoborate). Preferably the temperature is within the range of 140° to 180° C. for efficiency, economy, speed, and suppression of side reactions.

Pressure of the isomerization preferably is atmospheric down to about 1 mn. Hg. abs. (e.g., for removing alkanol from an alcohologen such as borate). Higher pressure can be used for the purpose of maintaining desired temperature.

Liquid phase conditions refer, of course, to the reactants. While the most effective catalysis is thought to be done by homogenous metal compounds, the catalyst can be introduced as a solid or as a solution of dissolved solid or solidly supported material. Reactants such as boric acid can be added as a solid if desired; their esters usually are liquid or will dissolve in the reaction mixture or can be rendered effectively in liquid phase by dissolution in an added organic solvent that is inert to the reaction, e.g., a liquid aromatic or aliphatic hydrocarbon preferably having a boiling range or boiling point for eventual removal at temperature not above about 250° C. at a useful operating pressure (1 mm. Hg. or above) and not boiling at a temperature too close to the allylic products to make separation therefrom especially difficult. Other alcohologen esters likewise are either miscible into the reaction mixture or will be dissolved by use of extraneous inert solvent for the instant purpose.

The most practical alcohologens for the instant isomerization are esters, particularly orthoborates (and metaborates, which convert into orthoborates in the presence of more than a mol of alcohol per mol of equivalent boric acid in the metaborate), as well as other Group III or IV metal compounds such as orthotitanates, zirconates, orthosilicates, aluminum alcoholates, carbonates, stannates (e.g., tin tetraisopropoxide) and carboxylates, lanthanum alcoholates, (e.g., lanthanum isopropoxide), and the like.

The least stable of these are the carbonates, hence they are less advantageous than the others. For this application the aluminum alkoxides are considered esters inasmuch as aluminum is amphoteric and its hydroxide will dissolve in aqueous caustic soda to form sodium aluminate. Elements in Groups IIIb, IVa, and IVb are preferred. Lanthanium operates in the process to convert geraniol directly to citronellol.

Such esters of alkanols, advantageously no higher than $C_{20}$ and preferably $C_4$-$C_8$ alkanols are used for transesterification with an allylic tertiary alcohol at broadly about 150°–250° C. and preferably 140°–180° C. to form allylic alcohologen either concurrently with the isomerizations occurring or previous thereto. Normal butanol or isobutanol are the preferred such alkanols for price, with the slightly more costly secondary butanol also being excellent technically for atmospheric pressure operation in many stages of the processing.

Esters of thiolcarboxylic acids are possible alcohologens also, but their cost and possibilities for forming malodorous compounds render them far less practical than the oxyesters listed above.

While alcohologens in the crude reaction product can be cleaved in many ways to yield alcohols, the best such way is by hydrolysis, using modestly elevated (80°–90° C.) temperature and base such as caustic soda if necessary. Cleaving also can be done by alcoholysis (with an alcohol such as methanol), and carboxylates could even be cleaved by reaction with ammonia or a primary or or secondary amine to liberate alcohol and form an amide.

Another valuable alternative to the aqeuous hydrolysis of the primary allylic borates, (produced by the instant process), in order to recover either boric acid crystals or boric acid aqueous solution, is alcoholysis so as to make another borate ester. Alcoholysis with alcohols either higher boiling or lower boiling than the allylic alcohols present (e.g., linalool, nerol, and geraniol) can be used. If higher boiling alcohols are used, then the allylic alcohols could be removed by distillation from the newly-formed borate esters of the higher boiling alcohols. Such borate esters of the higher boiling alcohols (such as lauryl alcohol and myristic alcohol) would be expected to have value as heat transfer fluids and fuel additives.

Alternately, the alcoholysis of the allylic borates, produced in instant process, could be carried out with a low boiling alcohol such as methanol. This methanolysis could be carried out by the addition of about 10–50 mols of methanol per mol of allylic borate esters followed by 30 min. reflux at atmospheric pressure, then by distillation at atmospheric pressure as described in U.S. Pat. No. 3,117,153. The distillate in the boiling range of 55° to 78° C. at atmospheric pressure will contain trimethylborate and methanol. This distillate can be separated by fractional distillation into a trimethylborate-methanol azeotrope fraction and a methanol fraction as described in U.S. Pat. No. 3,117,153. The trimethylborate-methanol azeotrope may be further treated by salting with lithium chloride or calcium chloride so as to prepare a pure trimethylborate fraction if desired.

Both trimethylborate and its methanol azeotrope are valuable articles of commerce and have uses such as borating agents and fuel additives. It is further expected that the recovered trimethyl borate, used in suitable excess to borate say, linalool, would be a useful borating agent in the instant process for producing such starting tertiary allylic alcohologen.

While the two schemes immediately above have been described specifically in connection with boric acid and orthoborate esters, similar use of higher ($C_{12}+$) aluminum alcoholates, and zirconates, orthosilicates, and titanates of the higher boiling alcohols such as lauryl and higher is expected to be possible.

While hydrolysis is a very useful reaction for converting allylic alcohologen reaction products into corresponding alcohols, many other reactions of such alcohologens are possible. Oppenauer oxidation thereof with a carbonyl compound is possible. Thus, aluminum geraniolates and nerolates (preferably substantially free from alkanol radicals and admixture with free alkanol) are reactable with an excess of acetone at temperature of 55° to 60° C. (or higher under pressure) to yield pseudoionone (via intermediate citral), and are reactable with furfural at temperature about 40° C. to yield citral (note U.S. Pat. No. 4,055,601 to W. J. Ehmann).

Other possible reactions employing allylic alcohologen products would be amination with ammonia or an amine, and hydrolysis followed by oxidation, e.g., with aqueous chromic acid solution.

Another unique and valuable isomerization related to the instant invention concerns the preparation of high purity linalool from nerol and/or geraniol. Linalool, produced from a-pinene, contains several byproducts such as the plinols and fenchol which are difficult to remove by fractional distillation. The distillation equipment used to prepare a very high purity, perfume grade linalool requires a substantial capital investment and operating costs because of this. However, linalool can give in high conversion, as shown in this specification, nerol and geraniol. Both of these alcohols are readily separable from each other by fractional distillation. Traditionally, geraniol has always been the more valuable of these two primary allylic alcohols because of its preferred odor and because of the greater ease with which it can be processed into valuable products such as citronellol, citronellal, and citral. Nerol, on the other hand, is less valuable. Thus the possibility of its conversion to linalool can be commercially attractive. Linalool is the lowest boiling of the three allylic alcohols which are produced in the instant metal catalyzed isomerization process. Its removal from the reaction equilibrium can be achieved by carrying out an isomerization of nerol (and/or geraniol) in a vessel fitted with a distillation column capable of efficiently separating linalool from nerol and/or geraniol. This technique could be employed readily in a commerical processing unit except for the fact that prolonged reaction time of about 4 to 12 hours will lead to the formation of dimeric products promoted by the reaction of the primary alcohols present with the vanadium or other catalytic metal present.

Utilization of neryl and/or geranyl borate esters as starting materials for the preparation of linalool are thus very attractive because of the chemical stability of these esters in the presence of such active metal-bearing isomerization catalysts such as the orthovanadic esters. These catalytic esters would be in equilibrium with the linalyl borate esters (or other linalyl ester alcohologens), such equilibrium being effected by the active metal catalyst. The linalool then could be conveniently displaced from its borate ester by the addition of a stable alcohol that will not isomerize in the presence of the active metal catalyst. Such an alcohol preferably should be higher boiling than linalool. Examples of such alcohols would be decanol, lauryl alcohol, myristic alcohol and the like.

Another embodiment leading to the production of relatively pure linalool by the reverse isomerization of nerol and/or geraniol involves reacting a higher boiling secondary or tertiary alcohol with boric acid to form a borate ester. A vanadium catalyst is introduced into the reaction mass, for example trihexylorthovanadate, in a catalytic amount. Nerol (or geraniol) a primary alcohol is added which then displaces the higher boiling secondary or tertiary alcohol from the borate ester to yield neryl (or geranyl) borate. The neryl (or geranyl) borate is isomerized in the presence of the vanadium catalyst to produce an equilibrium containing a small amount of linalyl borate. The higher boiling secondary or tertiary alcohol then displaces linalool, a tertiary alcohol, from the linalyl borate to liberate linalool. Linalool which has the lowest boiling point is removed by fractional distillation. Continuous introduction of nerol (and/or geraniol) at a rate equivalent to linalool production enables continuous production of relatively high purity linalool.

Another aspect of this method for the production of linalool from nerol and/or geraniol through the intermediacy of a borate or like quite stable ester (silicate, aluminate, titanate, stannate or zirconate) is based on the mode where the isomerization is carried out in the presence of such stable ester of a primary (or secondary) alcohol such as decanol, lauryl alcohol, or myristic alcohol. The operation for convenience will be described with borate esters from here on. The initial borate ester charge is trilauryl borate. In such a scheme the active metal catalyst would dissolve in the reaction mixture at 160° to 180° C. Nerol and/or geraniol then could be fed into the reaction medium at a controlled rate, and therein react with the lauryl borate so as to form neryl borate linkages. Metal catalyzed isomerization of such neryl borates will produce the corresponding linalyl derivatives. Linalool will be displaced from the borate by the primary alcohols, nerol and lauryl alcohol, present.

The free linalool so formed will be removed through the fractional distillation column situated over the reactor. The pressure throughout the process would be reduced (10–100 mm. Hg abs.) so as to varporize linalool from the reaction medium adequately at temperature between 140° and 180° C.

The whole value of this mode of operation for the production of linalool from nerol and/or geraniol resides in the fact that prolonged treatment, typical of reference processes, or free nerol and/or geraniol in the presence of the metal isomerization catalyst is avoided. Rather this "reverse" isomerization is carried out primarily through stable alcohologens which are chemically more stable under the reaction conditions.

It should be noted specifically that, of the reactants and solvents used in the instant processing, only the allylic tertiary alcohol such as linalool need be consumed (except for very small losses), and this goes to make allylic primary alcohols (such as geraniol and nerol from linalool) and allylic secondary alcohols (such as trans-piperitol from trans-2-menthene-1-ol). Even catalyst that remains in boric acid solution remains for reuse. While recovery of other catalyst or catalyst-forming material is possible (from filter cake and/or distillation residues), it usually is not economic to do so here.

The following examples show various ways in which this invention was practiced in glass, but they should not be construed as limiting the invention. For the most part they outline laboratory development that was done to arrive at best modes for operating the two major aspects of this invention. Such modes are described in connection with the drawings hereinabove. In this specification all parts are parts by weight, all percentages are mol percentages, and all temperatures are in degrees Celsius unless otherwise expressly indicated.

The laboratory kettle used for the isomerization was a 3-necked glass flask fitted with a thermowell for temperature sensing, an agitator, a heating mantle, and a Barrett trap for accepting vapor from the flask directing it upwardly through a short column topped with an indirect water-cooled condenser which allowed condensate to drain downwardly into the column and ultimately into a vertical leg that could be tapped of accumulated liquid, particularly distinct aqueous layers. Unless otherwise expressly noted, the condenser was vented to atmosphere. In those isomerization runs which are indicated to have been done at reduced pressure, the condenser vapor outlet was connected to a vacuum line.

Subatmospheric pressure distillations for separating and/or reclaiming alkanol were used in several of the runs. In such instances the trap was replaced by a short 8-inch Vigreaux fractional distillation column. Vapors from a distilling column entered the condenser, and condensate from the condenser could be directed to reflux the top of the column and/or to draw off distillate product. The vapor outlet of the condenser was connected to a vacuum line for obtaining sub-atmospheric pressure as needed. Crude and intermediate product analyses were done by gas chromatography of aqueous NaOH-hydrolyzed samples to measure resulting alcohols. The mol ratio of geraniol to nerol in hydrolyzed samples indicated typically 62 parts geraniol per 38 parts of nerol. Unless otherwise expressly indicated, the linalool charged to isomerization was a technical grade of about 95% purity, the remainder being mostly a plinol. I.R. analysis also was used in places.

The following examples illustrate isomerization reactions whereby an allylic alcohol of one degree (primary, secondary, or tertiary) can be isomerized as the alcohologen to an allylic alcohologen of a different degree (tertiary, secondary, or primary) and the alcohologen cleaved to recover, for example, the corresponding allylic alcohol. The alcohols are classified as primary (1°), secondary (2°), or tertiary (3°) depending upon the nature of the carbon atom holding the hydroxyl group. (See Morrison and Boyd "Organic Chemistry", Second Edition, 1966, Pages 160-161—Copy attached).

EXAMPLE 1

The flask (kettle) was charged with the following: 154 gm. linalool, 100 cc. toluene, 163 gm. n-butanol, 62 gm. boric acid, and 0.3 gm. ammonium metavanadate. This material was agitated and warmed to maintain 160° C. for 8 hours with consequent distillation of organic material and water at atmospheric pressure using the trap. A sample of the product indicated that 82.9% of the allylic alcohols present were geraniol and nerol.

Then 308 gm. of fresh linalool and 25 cc. of fresh toluene were added to the flask and the operation continued in the same way for 8 more hours at 160° C., followed by a still further 8 hours with the kettle temperature gradually reaching 180° C. A sample indicated that 72.4% of the allylic alcohols present were geraniol and nerol.

The crude isomerized batch was worked up by agitation for 4 hours at 60° C. with 55 gm. of tap water, adding 200 gm. more tap water and agitating at 80°-90° C. for 15 more minutes, finally adding and mixing with the batch an additional 10 cc. of tap water, then settling the mixture in a separatory funnel warmed with heat lamp and draining off a water (lower) layer. The oil layer remaining was washed twice, each time with 50 cc. of tap water. The lower layer and resulting washings were combined, filtered to remove vanadium-bearing sludge, and reserved for reuse of their boric acid, etc., values in subsequent operations.

The washed oil layer was submitted to fraction distillation at reduced pressure using the Vigreaux column described above. A gram of potassium stearate was mixed with the distillant. Initial distillation was done at 100 mm. Hg. abs. for the bulk of the operation. Stripping of the residue was done first at 1 mm. Hg. abs. and ultimately at 0.2 mm. Hg. abs. The combined water layer and water washings were reserved for reuse.

The combined water layer and water washings were used in an operation like that of Example 1, except that most of the water from such recycle was removed by azeotroping with toluene before any linalool was charged to the flask. The product allylic alcohols were 65% geraniol and nerol (24.5% nerol and 40.5% geraniol) and 35% linalool. In subsequent operations with greater alkanol removal as much as about 90% of the allylic alcohols in the product were geraniol and nerol.

EXAMPLE 2

Linalool, 154 g., and 50 cc. of toluene were added to the flask fitted with the Barrett moisture trap. The solution was refluxed at atmospheric pressure and brought to 160° C. by removal of water and finally of toluene. The reaction was then cooled to 90° C. at which point were added 1.5 g. of the orthovanadate ester of triethanolamine and 77 g. (⅓ mol/mol linalool) tri-sec-butyl borate. The reaction was then heated and held at reflux at atmospheric pressure at 160° C. by removal of, as necessary, toluene and sec-butyl alcohol.

A sample was removed after 4 hours at 160° C. It contained a mol ratio of linalool to citral to nerol plus geraniol of 30.7 to 0.3 to 69.0. After 8 hours, the corresponding ratio was 22.3 to 1.7 to 75.9. Only a trace of dimeric products were observed by gas chromatography. Even less citral is formed with the use of other vanadate esters, e.g. trihexyl vanadate.

The reaction was repeated under the same conditions except that no tri-sec-butyl borate was used. The ratio of linalool to citral to nerol plus geraniol obtained was as follows:

| Hours | Linalool | Citral | Nerol Plus Geraniol |
|---|---|---|---|
| 2.5 | 70.3 | 2.4 | 27.3 |
| 4 | 62.9 | 4.8 | 32.3 |

| Hours | Linalool | Citral | Nerol Plus Geraniol |
|---|---|---|---|
| 8 | 56.0 | 13.4 | 30.6 |

Substantial amounts of dimeric products were observed to have formed (using chromatography). The 8-hour product was steam distilled so as to separate the alcohols from the non-volatile dimeric residue; the amount of such residue was found to be 24.4%.

These data not only show the utility of the boration technique in greatly improving the conversion of linalool to nerol plus geraniol, but also show its valuable protecting effect. Little or no citral is formed and the dimers loss is much reduced; typically the loss to dimers at high conversion to nerol plus geraniol is about 5–7%.

EXAMPLE 3

A flask was charged with 50.0 g. of practically pure linalyl dibutyl borate and heated to 160°. To the hot liquid was added 1.0 g. of triethanolamine orthovanadate (OVTEA), and the mixture was stirred for 2 hrs. at 160°–162°. The product was then cooled and hydrolyzed with 100 ml. of 5% aqueous sodium hydroxide. Analysis of the allylic alcohols showed the product to contain 16.95% linalool, 32.80% nerol and 50.26% geraniol. The linalyl dibutyl borate was made by reacting one mol of linalool having at least 95% purity with 1.1 mol of tributyl borate under reduced pressure (100 mm. Hg. abs.) to remove butyl alcohol at 140° C., then further heated at 140° C. under 10 mm. Hg. abs. to remove excess tributyl borate and virtually all other volatile materials.

EXAMPLE 4

Linalool, 77 g., of about 95% purity and 50 cc. toluene were added to the flask fitted with the trap. The solution was then heated to reflux at atmospheric pressure so as to remove traces of water. Toluene was then removed until the flask contents temperature reached 160° C. at reflux. The solution was cooled to 100° C. and then were added 0.75 g. trihexylorthovanadate and 68 g. methyl benzoate.

The reaction was then heated at atmospheric pressure in a conventional manner with 25% sodium hydroxide solution so as to hydrolyze the benzoate esters present. Analysis of the hydrolysis product by gas chromatography indicated that 45.3% of the allylic alcohol present was linalool and 54.7% was nerol plus geraniol.

EXAMPLE 5

Linalool, 77 g. of about 95% purity and 50 cc. toluene were added to the flask provided with agitation and a distillation head. The solution was heated to reflux and a portion of the toluene was removed (so as to remove traces of water) up to a pot temperature of 160° C. The reaction was cooled to 90° C. and then were added 0.8 g. trihexylorthovanadate and 65 g. diethyl carbonate. The reaction was then heated to reflux giving a pot temperature of 120° C. Periodically, small portions of the distillate were removed so as to keep the distillate temperature greater than 110° C. After a total of 31 hours heating at 120° C., analysis of a sample of flask contents indicated the presence of nerol plus geraniol: neryl and geranyl ethyl carbonates:linalool to be in the ratio of 24.9:25.2:49.9. These ratios show that a substantial amount of nerol and geraniol were removed from the equilibrium by transesterification with diethyl carbonate.

The reaction mixture was heated at reflux under atmospheric pressure in a conventional manner with sufficient aqueous 25% sodium hydroxide solution so as to hydrolyze the carbonate esters present. The total allylic alcohols found were about 50% nerol and geraniol and 50% linalool.

EXAMPLE 6

Linalool, 18.5 g., of about 95% purity, 40 g. n-octyl acetate and 50 cc. toluene were added to the flask fitted with the trap. The solution was brought to atmospheric pressure reflux at 140° C. by removal of traces of moisture and toluene. The solution was sampled for gas chromatographic analysis which indicated 27.4% toluene, 49.6% n-octyl acetate and 21.7% linalool.

To the cooled solution was added 0.6 g. trihexylorthovanadate. The reaction was then heated at 140° C. for 28 hours. Gas chromatographic analysis of the reaction showed 26.2% toluene, 39.9% n-octyl acetate, 6.5% linalool, 10.1% n-octanol, 3.2% nerol plus geraniol and 11.6% neryl plus geranyl acetates. (No correction factors were introduced into this analysis to take into consideration the difference in response of the octyl acetate and octanol with the responses of linalool, nerol plus geraniol and neryl plus geranyl acetates.)

The ratio of linalool to the total of nerol plus geraniol and their acetates is 30.5 to 69.5.

Hydrolysis of the esters in a conventional manner would produce the corresponding allylic alcohols, linalool, nerol, and geraniol.

EXAMPLE 7

Linalool, 15.4 g., and 25 cc. toluene were added to a 100 ml. 3-neck flask provided with the moisture trap. The solution was heated at atmospheric pressure so as to remove traces of moisture and eventually bring the kettle temperature to reflux of 140° C.

To the solution that had been cooled to 100° C., was added 20.8 g. tetraethyl silicate and 0.2 g. trihexylorthovanadate. The reaction was then brought to a kettle temperature at atmospheric pressure reflux of 160° C. by removal of toluene and displaced ethanol. After 4 hours at 160° C. analysis of the batch indicated the substantial conversion of linalool to neryl and geranyl triethyl silicates. The ratio of linalool to nerol plus geraniol to neryl plus geranyl triethyl silicates obtained was 3.3 to 2.3 to 94.4.

Hydrolysis of the silicate esters in the reaction products by refluxing it with aqueous 50% sodium hydroxide solution yielded crude alcoholic product for purification.

EXAMPLE 8

Linalool, 41 g., was placed in a 500 ml. one-neck flask provided with a polytetrafluorethylene-coated magnetic stirrer and fitted to a condenser and distilling head. The linalool was then heated to 140° C. at 100 mm. Hg. abs. pressure so as to dry it. After one hour, the flask was cooled to about 90° C., and to it was added 110 g. aluminum isopropylate 50% in toluene. An 8" long by 1" diameter Vigreaux column was then fitted to the flask as previously described.

The flask was then heated at atmospheric pressure to a temperature of 120° C. so as to provide a distillate of 15 g. which had a boiling range of 82–83° C.; this was thought to be mainly toluene.

The flask then was cooled, placed under 100 mm. hg. abs. pressure, heated to 120° C. so as to provide a distillate of 51 g. having a boiling range of 45 to 52° C. The flask was cooled and a sample of the solution was analyzed by infrared spectroscopy which indicated that substantially no free linalool was present, but instead linalool had displaced a substantial amount of isopropanol from combination with aluminum.

To the reaction mixture then was added 0.4 g. trihexylorthovanadate. The reaction then was held at 140° C. for 36 hours. I.R. analysis of the clear solution indicated the substantial absence of any OH absorption typically found at 3500 cm$^{-1}$. Hydrolysis of the sample with aqueous 50% sodium hydroxide solution provided an alcohol-oil phase, which by gas chromatographic analysis indicated the presence of 29.4% linalool, 22.1% nerol and 38.9% geraniol. The ratio of linalool to nerol plus geraniol was 32.5 to 67.5.

EXAMPLE 9

Linalool, 154, g., and 50 cc. of toluene were added to the flask provided with the trap. The solution then was refluxed at atmospheric pressure so as to remove traces of water. The solution was cooled to 90° C., at which point 1.5 g. trihexylorthovanadate was added. Then, the reaction was heated to 160° C. with removal of toluene at atmospheric pressure and held at 160° C. for one hour. Analysis at this point indicated a ratio of linalool to nerol plus geraniol of 78 to 22.

Then 136 g. of 50% aluminum isopropoxide in toluene was added after having cooled the reaction to about 120° C. The reaction was heated to reflux at 140° C. After 5 hours of heating at 140° C., a sample was removed and washed with 25% sodium hydroxide solution prior to analysis by gas chromatography which indicated a ratio of linalool to nerol plus geraniol of 61 to 39.

One hundred cc. of toluene were then added, and toluene and isopropanol were distilled at atmospheric pressure out of the reaction mass to again reach 140° C. The reaction was held at 140° C. for 10 hours, at which point analysis indicated a ratio of linalool to nerol plus geraniol of 25 to 75.

Again, 100 cc. of toluene were added to the reaction, which was then heated to reflux at 140° C. so as to remove substantially any isopropanol present. The reaction was held at reflux at 140° C. for 4 hours longer. Analysis of the reaction as above indicated a ratio of linalool to nerol plus geraniol of 13 to 87.

For demonstrating a convenient aspect of the formation of the aluminum alkoxides of nerol and geraniol to displace the equilibrium, to the reaction mass was then added 600 cc. dry acetone. The reaction was then heated at reflux at atmosphere pressure for 3 hours. Analysis of the crude reaction mixture by gas chromatography indicated a ratio of linalool to nerol plus geraniol to cis- and trans-pseudoionones of 15.0 to 43.6 to 41.4.

The reaction was then treated at room temperature with 350 cc. of H$_2$SO$_4$ solution and washed two times with 300 cc. of water. The recovered oil phase was then distilled at reduced pressure (10 mm. to 1 mm. Hg. absolute descending during the distillation) through a vigreaux column to provide a distillate which by gas chromatographic analysis contained 13.5 g. linalool, 44.3 g nerol plus geraniol, and 41.4 g. cis- and trans-pseudoionone.

EXAMPLE 10

Linalool, 154 g., and 50 cc. of toluene were added to the flask provided with the trap. The solution was brought to reflux at atmospheric pressure so as to dry the linalool. then toluene was removed until a pot temperature of 160° C. was reached at reflux.

The solution was briefly cooled for the addition of 1.5 g. trihexylorthovanadate catalyst, then held at reflux at atmospheric pressure for 1 hour. Gas chromatographic analysis indicated a ratio of linalool to nerol plus geraniol of 81 to 19.

To the reaction batch then was added 100 g. titanium tetraisobutoxide. The reaction was brought to reflux at about 155° C. by distillation of the isobutanol displaced in the reaction. After 5 hours at reflux a sample was removed and steam distilled at atmospheric pressure so as to hydrolyze the titanium alkoxides and to separate the alcohols present. Gas chromatographic analysis of the oily alcohol (upper) phase indicated a ratio of linalool to nerol plus geraniol of 75 to 25.

To the cooled reaction batch was added 100 cc. of toluene. The reaction was brought to 155° C. by distilling off toluene and co-distilling some isobutyl alcohol. The batch then was heated at reflux (155° C.) at atmospheric pressure for 7.5 hours, at which time gas chromatographic analysis of a hydrolyzed sample indicated a ratio of linalool to nerol plus geraniol of 72 to 28. Evident also at this point was the presence of isogeraniols in the reaction product.

To the cooled reaction mixture was added another 100 cc. portion of toluene. Distillation then was used to bring the reaction to 155° C. and remove isobutanol. The reaction was held at 155° C. for 13 hours whereupon it was terminated.

A portion of the reaction was steam distilled to provide a crude product having a ratio of linalool to nerol plus geraniol to cis- and trans-isogeraniols of 62 to 25 to 13, respectively. The isogeraniols, while not known to be useful in perfumery, can be (like geraniol) hydrogenated to yield citronellol, a valuable perfumery material.

EXAMPLE 11

Nerolidol, of about 95% purity, containing a mixture of cis- and trans-isomers, 25 g., and 50 cc. of toluene were added to the flask provided with the moisture trap. The solution was refluxed under atmospheric pressure at 120° C. so as to remove any traces of water. The solution was cooled to 90° C., at which point 0.25 g. of trihexylorthovanadate and 26.0 g. of triisobutyl borate were added. The reaction was then brought to reflux at 160° C. by distillation of the toluene and isobutanol displaced in the reaction. After 8 hours at 160° C. a sample of the reaction was treated with dilute sodium hydroxide solution so as to hydrolyze the borate esters. Gas chromatographic analysis of the hydrolyzed sample indicated a ratio of nerolidols to farnesols of 19.4 to 80.6.

A corresponding reaction was carried out under identical conditions except that no triisobutyl borate or other like agent was added. After 8 hours at 160° C. the ratio of nerolidols to farnesols was 68.6 to 31.4.

EXAMPLE 12

Trans-2-Menthene-1-ol, 20 g., of about 93% purity, and 25 cc. of toluene were added to the flask provided with the moisture trap. The solution was brought to reflux at 155 to 160° C. under atmospheric pressure by removal of toluene and traces of water. The solution was then cooled to 100° C. at which point were added 0.2 g. trihexylvanadate and 16.5 g. tri-n-butyl borate. The reaction was heated to reflux at a pot temperature adjusted to 160° C. by removal of butanol and toluene through the distillation received. After 2 hours at reflux a sample was removed and hydrolyzed for gas chromatographic analysis (uncorrected for response factors) which indicated the presence of 1.8% toluene, 5.0% n-butanol, 4.8% p-menthadienes, 27.9% trans-2-menthene-1-ol, and 47.2% trans-piperitol.

The procedure was carried out again in exactly the same manner, except that no tri-n-butyl borate or like agent was used. After one hour at 160° C. there was a substantial amount of dehydration to form p-menthadienes. By gas chromatography the batch analyzed 21% toluene, 12.9% p-menthadienes, 36.9% trans-2-menthene-1-ol and 10.5% trans-piperitol.

These data show that the borating agent not only enabled the formation of more trans-piperitol, but also had a protective effect because stabilization against dehydration occurred as a consequence of the boration.

EXAMPLE 13

Linalool, 154 g., 100 cc. of toluene, 163 g. iso-butanol, 62 g. boric acid and 1.5 g. trihexylorthovanadate were added to the flask and brought to reflux at atmospheric pressure. The reflux temperature gradually rose from 94° to 145° C. until 54.2 g. of water had been separated from the toluene azeotrope. The reaction mass was then heated to 160° C. reflux at atmospheric pressure by removal of toluene and held at this temperature for 8 hours. Gas chromatographic analysis of a hydrolyzed reaction sample indicated that the allylic alcohol composition was 11.3% linalool and 88.7% nerol plus geraniol.

This reaction illustrates the beneficial effect obtained by the use of a one-to-one molar ratio of boric acid to linalool. If more linalool is added to the reaction at this point so as to change the corresponding ratio to one to three, then the reaction mass would isomerize in 8 more hours at 160° C. at atmospheric pressure to give a product which by gas chromatographic analysis of a hydrolyzed sample would have an allylic alcohol composition of about 25 to 30% linalool and 70 to 75% nerol plus geraniol. Higher conversion of linalool to nerol plus geraniol could then be achieved through removal of butanol from the reaction mass by distillation at reduced pressure.

The metal-containing isomerization catalyst useful in this allylic tertiary to allylic primary or secondary alcohol isomerization also appears to be effective for catalyzing the transesterification of a carboxylic acid ester with another ester, a carboxylic acid ester with an alcohol, or a carboxylic acid ester with another carboxylic acid. Polyacids, polyols, and polyesters are candidates here, as well as the monobasic or monofunctional materials. Vanadium and tungsten compounds are the most advantageous for such operation. If they are soluble readily in the reaction mixture this is of modest help. Where a product of the reaction can be removed, this, of course, helps to shift the equilibrium toward the residual product or products remaining in the reaction mixture. The following examples will illustrate typical such operations.

EXAMPLE 14

Two separate identical flasks were set up and into each was added 57 g. n-octyl acetate, 39 g. 98% geraniol and 50 cc. of toluene. Both were brought to reflux at 140° C. by removal of excess toluene from the Barrett trap. To one of the flasks, which had been cooled for a brief period, was added 0.5 g ammonium metavanadate. The two reaction vessels were refluxed under atmospheric pressure at 140° C. for 16 hours. At the end of this time a sample was removed from each. Gas chromatographic analysis of the reaction that had been carried in the absence of ammonium metavanadate showed virtually no reaction. Similar analysis, on the other hand, of the reaction that contained the vanadium catalyst showed the presence of 47.9% n-octyl acetate, 14.2% n-octanol, 6.9% linalool, 2.9% neryl acetate, 21.6% geranyl acetate, and 4.2% geraniol.

These data indicate that the vanadium catalyst is not only effective for the isomerization of allylic alcohols, but is also a very effective catalyst for promoting transesterification, in this instance between geraniol and n-octyl acetate.

EXAMPLE 15

To further demonstrate the surprising utility of orthovanadic esters in promoting ester exchange, the following reaction was carried out using esters of nonallylic alcohols.

To a flask fitted with a Barrett trap and condenser was added 25 g. n-octyl acetate, 25 g. n-hexyl butyrate, 0.5 g. trihexylorthovanadate, and 25 cc. of toluene. The contents of the reaction flask were then brought to reflux at 140° C. under atmospheric pressure by the removal of toluene from the Barrett trap. Gas chromatographic analysis of a flask sample after 8 hours reaction indicated that the reaction medium contained 31.3% n-hexylacetate, 18.2% n-hexyl butyrate, 17.8% n-octyl acetate, and 21.3% n-octyl butyrate.

A corresponding reaction was carried out in an identical manner except that no catalyst (trihexylorthovanadate) was used. After 8 hours of reaction no change in the composition of the flask contents could be detected by gas chromatography.

EXAMPLE 16

This example illustrates the use of a tin alkoxide as a protecting group for the isomerization of linalool to geraniol.

Linalool, 31 gm, of about 95% purity was refluxed with 100 cc toluene in a three-neck flask fitted with a stirrer and an 8" Vigreaux column. Above the column the reflux was cooled with a glass water condenser and allowed to return to the reaction flask. Any water present or formed during the reaction was removed from the distillate by use of a Barrett trap fitted between the column and condenser.

Toluene was removed from the distillate so as to provide a pot reflux temperature of 140° C. Infra-red analysis of the pot contents indicated the presence of linalool. Then 60 gm $(Bu_3Sn)_2O$ was added and the water liberated, about 1 cc, was removed in the distillate. After 2 hours reflux the pot contents were analyzed by infra-red spectroscopy. Substantially all the linalool had reacted to form linalyl tributyl stannate.

At this point, 1.0 gm trihexylvanadate was added and the reaction was heated at 140° C. for 6 hours and at 165 to 175° C. for 12.5 hours longer. A sample was removed and steam distilled so as to hydrolyze the stannate and remove the terpene alcohols from the tin residue Gas chromatographic analysis of the oil indicated a composition of 49.6% nerol/geraniol of the terpene allylic alcohols present.

EXAMPLE 17

This example illustrates the use of a zirconate as an alcohologen. The zirconate, like the titanate in Example 10 above appears to isomerize the nerol and geraniol to isogeraniols and to cause a small amount of citronellol formation.

A 250 ml three neck flask was equipped with a 10 cc Barrett trap fitted to water cooled, glass condenser. Agitation was provided by use of a Teflon coated, magnetic stirrer bar. To the flask were added 38.5 gm linalool, of about 95% purity and 50 ml heptane. The contents were refluxed 30 min. so as to remove water by azeotropic distillation. The solution was cooled briefly and to it was added 28.5 gm tetra-n-butyl zirconate. The solution was brought to reflux at 160° C. by removal of distillate from the Barrett trap. The solution was held at 160° C. for 2 hours at the end of which time a sample was removed and hydrolyzed prior to GC analysis. No isomerization of linalool to geraniol was observed.

After the addition of 1.0 g tri-n-hexylorthovanadate catalyst, the solution was then held at 160° C. reflux for 4 hours. A sample, which was removed and hydrolyzed for GC, was found to contain a ratio of linalool to nerol, geraniol and other isomeric primary alcohols of 53.6:46.4. These isomers such as cis- and trans-3,7-dimethyl-3,6-octadien-1-ol and 7-methyl-3-methylene-6-octene-1-ol are all useful for the production of the fragrance alcohols, citronellol and dimethyloctanol by the process of catalytic hydrogenation.

What is claimed is:

1. A process for allylic rearrangement which comprises: forming an isomerization reaction mixture containing allylic tertiary alcohologen; isomerizing said tertiary allylic alcohologen to primary and/or secondary allylic alcohologens by subjecting it to liquid phase catalytic isomerization conditions in the presence of a catalytic amount of a transition metal compound wherein the metal is selected from Group V, VI or VII of the Periodic Table said allylic tertiary alcohologen being an ester or alcoholate of an acid or a hydroxide of an element in Group III or IV of the Periodic Table, and cleaving the resulting isomerized allylic alcohologens.

2. The process of claim 1 wherein said tertiary allylic alcohologen has been preformed prior to said isomerizing.

3. The process of claim 1 wherein said tertiary allylic alcohologen is formed in said reaction mixture by a collateral reaction that is concurrent with the isomerizing of said alcohologen.

4. The process of claim 1 wherein said allylic tertiary alcohologen and said isomerized allylic alcohologens are hydrolysable esters.

5. The process of claim 4 wherein said esters are allylic borates.

6. The process of claim 5 wherein said allylic borates are formed by transesterification of an alkyl borate whose alkanol moiety, when liberated, has a boiling point below that of the allylic alcohols cleavable from the isomerized allylic borate present.

7. The process of claim 6 wherein said allylic borate is cleavable into primary and/or secondary allylic alcohol.

8. The process of claim 4 wherein said esters are aluminum allylic alcoholates.

9. The process of claim 4 wherein said esters are titanyl allylic esters.

10. The process of claim 4 wherein said esters are zirconyl allylic esters.

11. The process of claim 4 wherein said esters are allylic carbonates.

12. The process of claim 4 wherein said esters are allylic carboxylates.

13. The process of claim 4 wherein said esters are allylic orthosilicates.

14. The process of claim 4 wherein said esters are allylic stannates.

15. The process of claim 6 wherein said esters comprise a geranyl borate.

16. The process of claim 8 wherein said esters comprise an aluminum geraniolate.

17. The process of claim 9 wherein said esters comprise a titanyl ester of geraniol.

18. The process of claim 10 wherein said esters comprise a zirconyl ester of geraniol.

19. The process of claim 11 wherein said esters comprise a geranyl carbonate.

20. The process of claim 12 wherein said esters comprise a geranyl carboxylate.

21. The process of claim 13 wherein said esters comprise a geranyl orthosilicate.

22. The process of claim 14 wherein said esters comprise a geranyl stannate.

23. The process of claim 1 wherein the tertiary allylic alcohologen is a linaloologen, and the allylic alcohologens formed therefrom are geraniologenic and nerologenic.

24. The process of claim 23 wherein said linaloologen is formed from a butyl borate.

25. The process of claim 24 wherein said butyl borate comprises an isobutyl borate.

26. A process for preparing an allylic alcohol of one degree from an isomeric allylic alcohol of different degree characterized by forming an isomerization reaction mixture containing an alcohologen of said allylic alcohol of said different degree, isomerizing said alcohologen of said allylic alcohol of said different degree by subjecting it to liquid phase catalytic isomerization conditions in the presence of a transition metal compound isomerization catalyst, said alcohologen being an ester or alcoholate of an acid or hydroxide of an element of Group III or IV of the Periodic Table of Elements and cleaving the resulting isomerized allylic alcohologen.

27. A process for preparing an allylic alcohol of one degree from a corresponding allylic alcohol of different degree in accordance with claim 26 wherein said reaction mixture includes a nonallylic alcohol having a vapor pressure different from either said allylic alcohol of said one degree or said allylic alcohol of said different degree, and said isomerization is carried out at a temperature sufficiently high to distill off one of said nonallylic alcohol and said allylic alcohol of said one degree, said alcohologen being an ester or alcoholate of an acid or hydroxide of an element in Group III or IV of the Periodic Table.

28. A process for preparing a more volatile allylic alcohol of higher degree from less volatile allylic alcohol of lower degree in accordance with claim 27 wherein said nonallylic alcohol has a vapor pressure below that of the more volatile allylic alcohol of higher degree, and said isomerization reaction is carried out at a temperature sufficiently high to distill off said more volatile allylic alcohol of higher degree, said alcohologen being an ester or alcoholate of an acid or hydroxide of an element in Group III or IV of the Periodic Table.

29. A process as defined in claim 28 wherein the allylic alcohol of higher degree is a tertiary allylic alcohol.

30. A process as defined in claim 29 wherein the tertiary allylic alcohol is linalool.

31. A process as defined in claim 30 wherein the alcohologen of lower degree is an alcohologen selected from nerol, geraniol and mixtures of nerol and geraniol.

32. A process as defined in claim 31 wherein the alcohologen is a hydrolyzable ester.

33. A process as defined in claim 32 wherein the hydrolyzable ester comprises a borate ester of the selected alcohologen.

34. A process as defined in claim 32 wherein the hydrolyzable ester comprises an aluminum allylic alcoholate.

35. A process as defined in claim 32 wherein the hydrolyzable ester comprises a titanyl allylic ester.

36. A process as defined in claim 32 wherein the hydrolyzable ester comprises a zirconyl allylic ester.

37. A process as defined in claim 32 wherein the hydrolyzable ester comprises a allylic carbonate.

38. A process as defined in claim 32 wherein the hydrolyzable ester comprises a allylic carboxylate.

39. A process as defined in claim 32 wherein the hydrolyzable ester comprises a allylic orthosilicate.

40. A process as defined in claim 32 wherein the hydrolyzable ester comprises a allylic stannate.

41. A process a defined in claim 28 wherein the reaction is carried out at a sub-atmospheric pressue and at a temperature of from about 140° C. to about 180° C.

* * * * *